United States Patent
Wurtz et al.

(10) Patent No.: US 10,021,478 B2
(45) Date of Patent: Jul. 10, 2018

(54) IN-THE-EAR AUTOMATIC-NOISE-REDUCTION DEVICES, ASSEMBLIES, COMPONENTS, AND METHODS

(71) Applicant: Avnera Corporation, Beaverton, OR (US)

(72) Inventors: Michael Jon Wurtz, Lake Oswego, OR (US); Eric Sorensen, Portland, OR (US)

( * ) Notice: Subject to any disclaimer, the term of this patent is extended or adjusted under 35 U.S.C. 154(b) by 0 days.

(21) Appl. No.: 15/442,619

(22) Filed: Feb. 24, 2017

(65) Prior Publication Data

US 2018/0020281 A1 Jan. 18, 2018

Related U.S. Application Data

(60) Provisional application No. 62/299,558, filed on Feb. 24, 2016.

(51) Int. Cl.
*H04R 1/10* (2006.01)
*A61F 11/08* (2006.01)
(Continued)

(52) U.S. Cl.
CPC ............ *H04R 1/1083* (2013.01); *A61F 11/08* (2013.01); *G10K 11/178* (2013.01);
(Continued)

(58) Field of Classification Search
CPC .. H04R 1/1083; H04R 1/1016; H04R 23/006; H04R 2410/05; G10K 2210/3026; G10K 2210/3027; G10K 2210/3028
See application file for complete search history.

(56) References Cited

U.S. PATENT DOCUMENTS 6,625,287 B1 9/2003 Wurtz
6,704,428 B1 3/2004 Wurtz
(Continued)

FOREIGN PATENT DOCUMENTS

CN 104394490 A 3/2015
WO 2015/164287 A1 10/2015

OTHER PUBLICATIONS

International Search Report of PCT/US2017/019540, dated Jun. 30, 2017.

*Primary Examiner* — David Ton
(74) *Attorney, Agent, or Firm* — Eduardo E. Drake; Fantastic IP Consulting (57) ABSTRACT

Automatic noise-reduction (ANR) headsets include circuitry that cancels or suppress undesired noises. Recent years have seen the emergence of in-the-ear (ITE) earphones that incorporate ANR technology; however, designing them to function well usually entails many design tradeoffs, such as using larger ear nozzles that are uncomfortable to obtain desired noise reduction or that require added structures to hold the earphones to a user ear. To avoid these tradeoffs, the present inventors devised, among other things, an exemplary ITE ANR earphone that places its error measurement microphone in the ear nozzle that connects the driver front acoustic volume to a user ear canal. This placement allows use of a narrower more comfortable ear nozzle without compromising noise reduction and without requiring added holding structures. Moreover, the narrower ear nozzle also lowers the likelihood that the ANR circuitry will become unstable and produce undesirable noise.

19 Claims, 7 Drawing Sheets

(51) Int. Cl.
*H04R 23/00* (2006.01)
*G10K 11/178* (2006.01)

(52) U.S. Cl.
CPC ....... *G10K 11/1782* (2013.01); *H04R 1/1016* (2013.01); *H04R 23/006* (2013.01); *G10K 2210/1081* (2013.01); *G10K 2210/3026* (2013.01); *G10K 2210/3027* (2013.01); *G10K 2210/3028* (2013.01); *H04R 2201/003* (2013.01); *H04R 2410/05* (2013.01)

(56) References Cited

U.S. PATENT DOCUMENTS

| | | | |
|---|---|---|---|
| 7,317,802 B2 | 1/2008 | Wurtz | |
| 7,668,308 B1 | 2/2010 | Wurtz | |
| 8,320,591 B1 | 11/2012 | Wurtz | |
| 8,385,560 B2 | 2/2013 | Solbeck et al. | |
| 8,487,812 B1 | 5/2013 | Wurtz | |
| 8,682,001 B2 | 3/2014 | Annunziato et al. | |
| 9,525,930 B2 * | 12/2016 | Parkins | H01Q 7/08 |
| 9,792,893 B1 * | 10/2017 | Gauger, Jr. | G10K 11/1788 |
| 9,837,066 B2 | 12/2017 | Wurtz | |
| 2006/0013410 A1 | 1/2006 | Wurtz | |
| 2010/0119076 A1 | 5/2010 | Monk et al. | |
| 2010/0272275 A1 | 10/2010 | Carreras et al. | |
| 2013/0272530 A1 | 10/2013 | Gauger, Jr. | |
| 2013/0315411 A1 * | 11/2013 | Annunziato | G10K 11/16 381/71.6 |
| 2013/0329902 A1 | 12/2013 | Bakalos | |
| 2013/0343564 A1 * | 12/2013 | Darlington | H04R 1/1016 381/74 |
| 2014/0226832 A1 * | 8/2014 | Shimizu | H04R 1/1016 381/74 |
| 2014/0294193 A1 * | 10/2014 | Tikander | H04R 3/02 381/74 |
| 2016/0196819 A1 | 7/2016 | Wurtz | |
| 2016/0293156 A1 * | 10/2016 | Yang | G10K 11/1784 |
| 2017/0013345 A1 | 1/2017 | Kumar et al. | |
| 2018/0020281 A1 | 1/2018 | Wurtz | |

* cited by examiner

IN-THE-EAR AUTOMATIC-NOISE-REDUCTION DEVICES, ASSEMBLIES, COMPONENTS, AND METHODS

COPYRIGHT NOTICE AND PERMISSION

A portion of this patent document contains material subject to copyright protection. The copyright owner has no objection to the facsimile reproduction by anyone of the patent document or the patent disclosure, as it appears in the patent and trademark office patent files or records, but otherwise reserves all copyrights whatsoever. The following notice applies to this document: Copyright © 2016, AVNERA CORPORATION.

This document, which incorporates drawings and claims, describes one or more specific embodiments of one or more inventions. These embodiments, offered not to limit but only to exemplify and teach the invention, are shown and described in sufficient detail to enable those skilled in the art to implement or practice the invention(s). Thus, where appropriate to avoid obscuring the invention(s), the description may omit certain information known to those of skill in the art.

TECHNICAL FIELD

Various embodiments of the invention relate generally to automatic noise reduction devices and methods.

BACKGROUND

Automatic noise-reduction (ANR) headsets typically include a voice microphone along with two earcups which are worn over the ears of users to enhance or protect their hearing in noisy environments, for example by shielding their ears from loud persistent noises or filtering out background noises that might interfere with speech or music. These headsets include ear speakers, one or more extra microphones, and ANR circuitry. The microphones sense sounds in certain frequency ranges, and the ANR circuitry attempts to cancel or suppress it by driving the ear speakers to vibrate in opposition to the undesired sounds.

Recent years have seen the emergence of in-the-ear (ITE) earphones that incorporate ANR technology. The size and weight constraints with these devices typically force manufacturers to compromise one performance trait in order to enhance another. These tradeoffs ultimately result in a device that is less than optimal.

For example, U.S. Pat. No. 8,682,001 to Annuziato et al. (Annunciato) advises that for adequate ANR functioning, lower acoustic impedance is of prime importance. Moreover, it further states that reduced impedance is best achieved through having a nozzle or port connecting a front cavity portion of the earphone to a user ear canal, with the nozzle not only having as large cross-sectional area as possible, but also having a high aspect ratio (cross-sectional area to length ratio.) To this end, Annunziato provides a nozzle portion of its earbud device that has a cross-sectional area of 10 square millimeters and length of approximately 10 millimeters. Unfortunately, these dimensions force users to trade comfort for effective noise reduction. Moreover, the larger cross-sectional area makes it impractical to use the popular silicone rubber and foam earbud tips that easily conform to various shapes and sizes of user ear canals and ultimately provide a better acoustic seal of the ear cavity and thus better noise reduction.

To avoid use of a wider uncomfortable nozzle, U.S. Pat. No. 8,385,560 to Solbeck et al. (Solbeck) uses a smaller one along with a narrow probe tube that extends between the microphone in the front cavity near the ANR driver (speaker) and the ear cavity. While this approach avoids the uncomfortable nozzle, it also has at least two negative side effects of its own. One side effect is that Solbeck's tube increases the likelihood that the ANR circuitry will become unstable (because of reduced phase margin) and thus create high pitched squeals in the ears of users. The other side effect is that the tube requires added circuitry or processing to adjust frequency response of the ANR circuitry, and this in turn increases the level of electronic noise users experience. These side effects are acceptable for Solbeck's objective of protecting user hearing and allowing basic communication, but not for ITE earphone users who desire a superior music and audio listening experience.

Accordingly, the present inventor has recognize a need for alternative devices that avoid or otherwise reduce the design compromises built into most conventional ITE ANR devices.

SUMMARY

To address one or more of these and/or other needs or problems, the present inventor devised, among other things, one or more exemplary systems, kits, methods, devices, assemblies, and/or components suitable for providing improved ITE ANR.

One exemplary embodiment includes an active noise reduction earphone that places its error measurement microphone in the port that connects the driver front acoustic volume to the ear canal. Placing the microphone in the port allows the microphone to more closely measure or sense what is happening in the ear canal compared to prior art methods that put the microphone in the driver front acoustic volume. In some embodiments, the microphone takes the form of a micro electro mechanical sensor (MEMS) microphone, and is oriented transverse, for example, perpendicular, to the direction of sound within this port. In still further embodiments, the microphone package includes one or more longitudinal flanges that slideably engage with corresponding grooves or slots on the interior of the port.

In contrast to conventional ITE ANR devices that require an uncomfortably sized ear-insertion port or that use a probe tube that increases likelihood of noise and squeals, the various embodiments of the present invention avoid these issues through novel placement of the feedback microphone within a comfortably sized port that fits into the user's ear canal. In one embodiment, the ear-insertion port has a cross-sectional area of approximately 3.3 square millimeters, which is only one third the 10 square millimeters used in conventional ITE devices that follow Annuziato. The effective length of the exemplary port is about 10 millimeters, with about 4 millimeters attributable to the flexible tip that the smaller ear-insertion port accommodates.

In addition to providing greater comfort without sacrificing ANR performance, a further advantage of placing the microphone within the ear insertion port is that it promotes or maintains ANR feedback loop stability during and after removal of the earphone from the user's ear. This is significant because the instability would likely reveal itself audibly as high pitch squeals to the user, which is not only unpleasant, but suggestive of poor quality and low value, a highly undersirable outcome for users who desire a quality listening experience.

BRIEF DESCRIPTION OF THE DRAWINGS

Various embodiments are described herein with reference to the following attached figures (Figs). These figures are annotated with reference numbers for various features and components, and these numbers are used in the following description as a teaching aid, with like numbers referring to the same or similar features and components.

DETAILED DESCRIPTION OF THE EXEMPLARY EMBODIMENT(S)

This document, which incorporates drawings and claims, describes one or more specific embodiments of one or more inventions. These embodiments, which are offered not to limit but only to exemplify and teach the invention, are shown and described in sufficient detail to enable those skilled in the art to implement or practice the invention(s). Moreover, where appropriate to avoid obscuring the invention(s), the description may omit certain information known to those of skill in the art.

Figure 1:
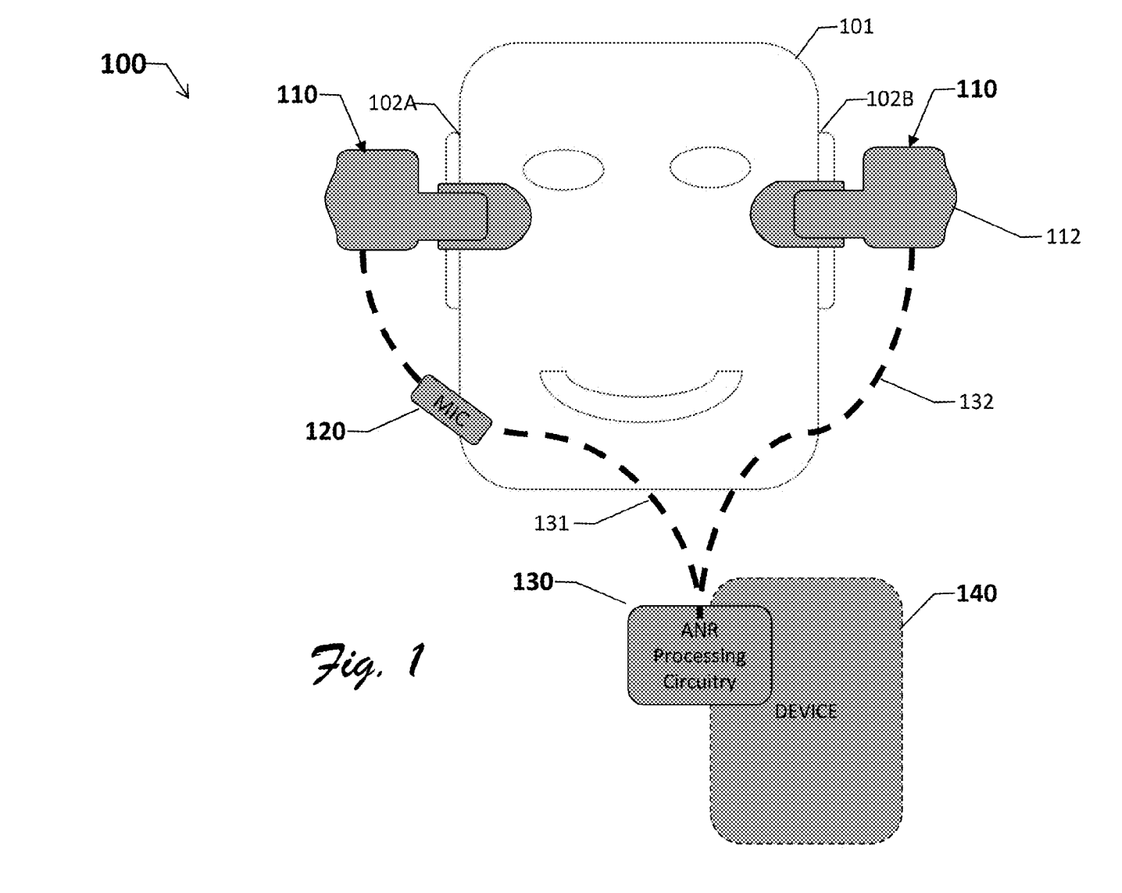
FIG. 1 is a block diagram of an exemplary in-the-ear (ITE) headset system or assembly 100 corresponding to one or more embodiments of the present invention.

FIG. 1 shows an exemplary in-the-ear (ITE) headset assembly or system 100 mounted in ears 102A and 102B of a user's head 101. Assembly 100 includes left and right ITE earpieces or earbuds 110A and 110B, an in-line microphone 120, and automatic noise reduction (ANR) or automatic noise cancellation (ANC) processing circuitry 130, and a host or external device 140. Earpieces 110A and 110B, are coupled via respective wired communication links 131 and 132 to ANR processing circuitry 130. Circuitry 130 may be a stand-alone component that cooperates with device 140, such as smartphone, laptop, tablet computer, or gaming counsel, or may be integrated into device 140. Also in some embodiments, ANR processing circuitry 130 includes adaptive ANR processing, such as the type described in U.S. patent application Ser. No. 15/069,271 filed Mar. 4, 2016, which is incorporated herein by reference.

Figure 2:
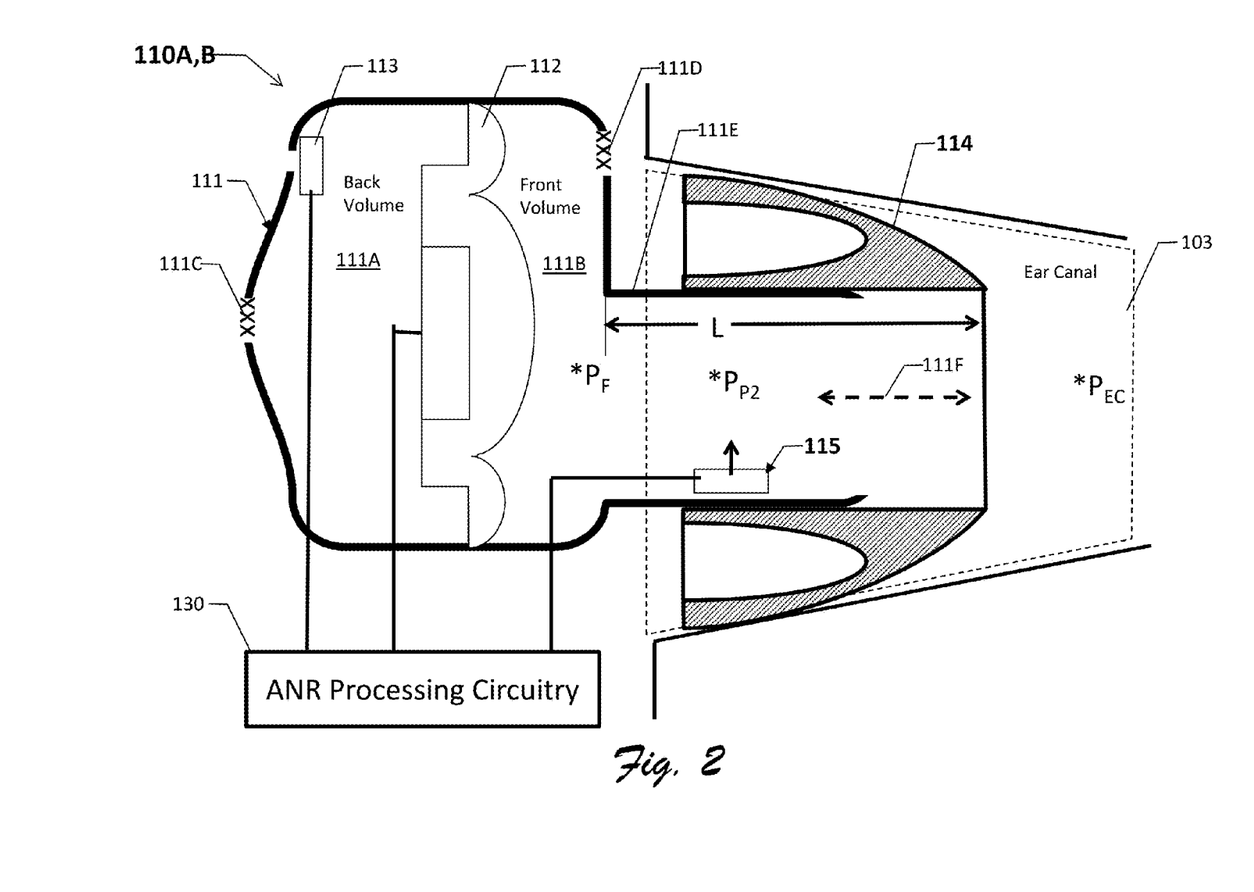
FIG. 2 is a conceptual cross-sectional view of an exemplary ITE earphone portion of the FIG. 1 assembly, corresponding to one or more embodiments of the present invention.

FIG. 2 shows a conceptual diagram of earpiece 110A, which is substantially identical in form and function to earbud 110B. Earbud 110A, includes a main housing 111, an ANR driver 112, a feedforward ambient microphone 113, an ear adapter tip 114, and a feeback error microphone 115.

Housing 111 is divided interiorly into a back cavity 111A and a front cavity 111B by ANR driver 112, with back cavity 111A vented to atmosphere via a back cavity vent 111C and front cavity 111B vented to atmosphere via a front cavity vent 111D. Within the back cavity is feedforward ambient microphone 113, which, provides a signal to ANR processing circuitry 130 generally representative of ambient noise to be cancelled by the ANR processing circuitry. Front cavity 111B includes an ear-insertion port or nozzle 111E.

Nozzle 111E, shown inserted into user ear canal 103, has a uniform nominal cross-sectional area of approximately 3.3 millimeters and length L of approximately 6.0 millimeters in the exemplary embodiment. These dimensions allow termination of the nozzle with an adapter tip 114, which effectively extends the length of the nozzle to 10 millimeters. The combination of the adapter tip and the nozzle dimensions provide an acoustic mass ($M = \rho L/A$) of approximately 2500 $kg/M^4$, where $\rho$ is the density of air, L is the effective length of the nozzle with the adapter tip, and A is the open cross-sectional area of the nozzle (assuming the adapter tip provides substantially the same open cross-sectional area.) Without the adapter tip, the acoustic mass is approximately 2200 $kg/M^4$. The magnitude of the mass impedance, $|z|$ of the nozzle is generally computed from the product of the M as the relevant frequency f as $$|z| = Mf.$$

Some embodiments provide nozzles with an acoustic mass and a mass impedance that is in the range of plus or minus 20% of those in this exemplary embodiment. Note that while the mass impedance of the port is significant, even more important to cancellation performance is the impedance from the microphone to the ear, not that of the port itself, along with adaptive ANC.

Adapter tip 114, which may be formed of silicone rubber or pliable material for example, includes an inner sleeve portion 114A that not only elastically engages with an end portion of nozzle 111E, and an outer dome portion 114B that forms a tight seal with user ear canal 103. The pliable nature of silicone rubber or in some embodiments foam allows the adapter tip to fit a wide variety of user ear canal shapes and sizes.

Within nozzle 111E is feedback error microphone 115. Microphone 115, for example MEMS microphone, is positioned perpendicular to the direction of acoustic energy 111F within the nozzle, providing grazing incidence with the acoustic energy. In some embodiments, other transverse orientations are used.

In operation, microphone 115 provides a summation of the total acoustic energy within the ear canal or cavity 103 to ANR processing circuitry 130. ANR processing circuitry 130, which may be digital or analog in nature, also receives an earphone audio signal from a device, such as smartphone, music player, or other electronic audio source. In some embodiments, the device may host the ANR processing circuitry. In response to ambient noise signal from feedforward microphone 113, ANR processing circuitry generates a noise cancellation signal and sends a mix or sum of the cancellation signal and the earphone audio signal to ANR driver 112, which produces acoustic energy cancelling substantial portions of the perceived ambient noise and providing an acoustic representation of the earphone audio signal.

Notably, placement of feedback error microphone 15 within nozzle 111E, the ear-insertion port, allows the microphone to more closely measure or sense acoustic energy (sound pressure) in the ear canal compared to conventional ITE ANR devices that put the microphone in the driver front acoustic volume outside their nozzles. This can be a major advantage in embodiments that employ adaptive ff filters as the filters need to estimate the canal pressure closely if cancelation is to be achieved after a adaptive filter is realized. Moreover, the nozzles of these conventional devices have cross-sections that are too large for fitting comfortably within a user's ear canal and thus require added structures for secure attachment to the user's ear. Additionally, microphone placement within the nozzle bypasses the need for using a probe tube that compromises ANR loop stability, thus providing a device with lower likelihood of side-effect noise and squeals.

Figure 3:
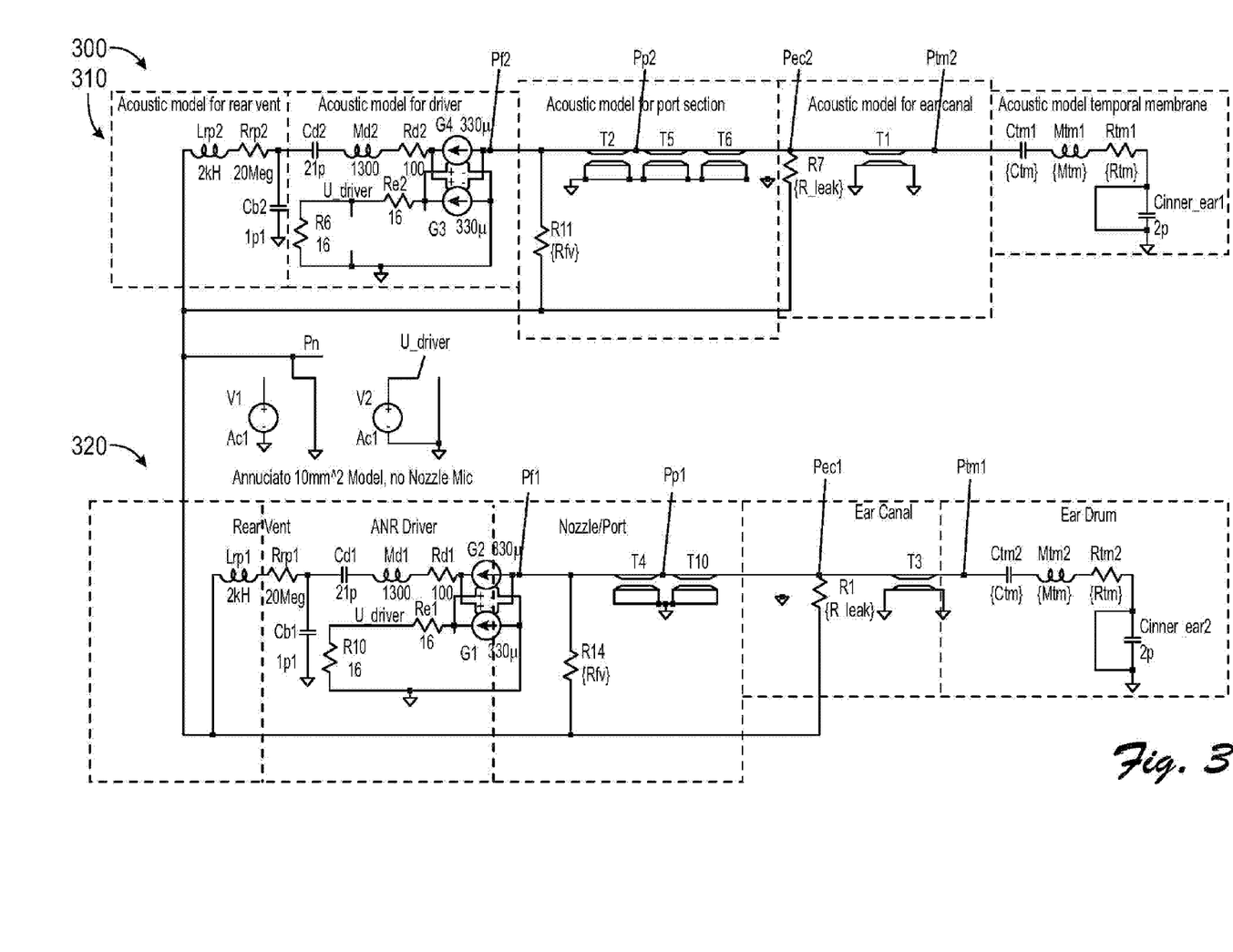
FIG. 3 is an equivalent electrical model of a portion of FIG. 2, corresponding to one or more embodiments of the present invention as well as a conventional.
Figure 4:
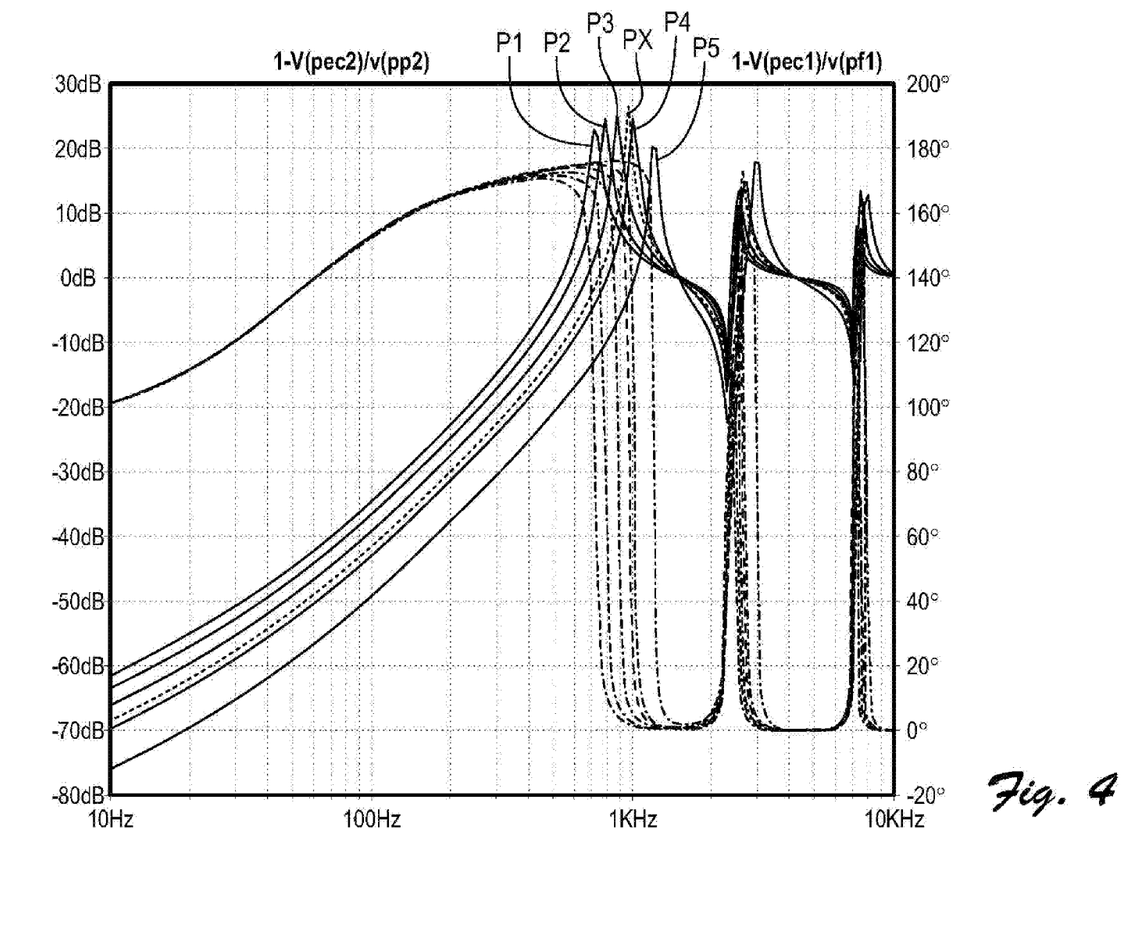
FIG. 4 is a graph showing relative cancellation performance of one embodiment of the present invention with various feedback mic placements within an ear insertion port.

FIG. 3 shows an exemplary electrical model of the FIG. 2 system, which was used to simulate performance of two ANR earbuds, one based on Annunciato's 10 millimeter long by 10-square-millimeter nozzle and conventional error microphone placement, and the other based on the exemplary embodiment's 10-millimeter long by 3.3-square-millimeter nozzle cross-section. FIG. 4 shows 5 curves based on the exemplary implementation and 1 red curve based on the Annunciato 10-square-millimeter implementation, with each curve presenting the the ratio of the pressure in the ear cavity Pec to the feedback pressure Pmic—a measure of how well cancellation of the pressure at the feedback microphone will correlate to cancellation in the ear canal. Each of the five green curves stem from at different positions of the error microphone within the 3.3-square-millimeter nozzle, specifically at the very back of the nozzle (P1), at 25% (P2), 50% (P3), 75% (P4), and at the end of the port (P5). The red curve PX indicates performance of the Annunicatio model. Ultimately, the graphs indicate in compelling fashion that placement of the error microphone within the nozzle, in contravention of conventional wisdom, allows one to bypass the design tradeoffs associated with a larger nozzle.

Figure 5:
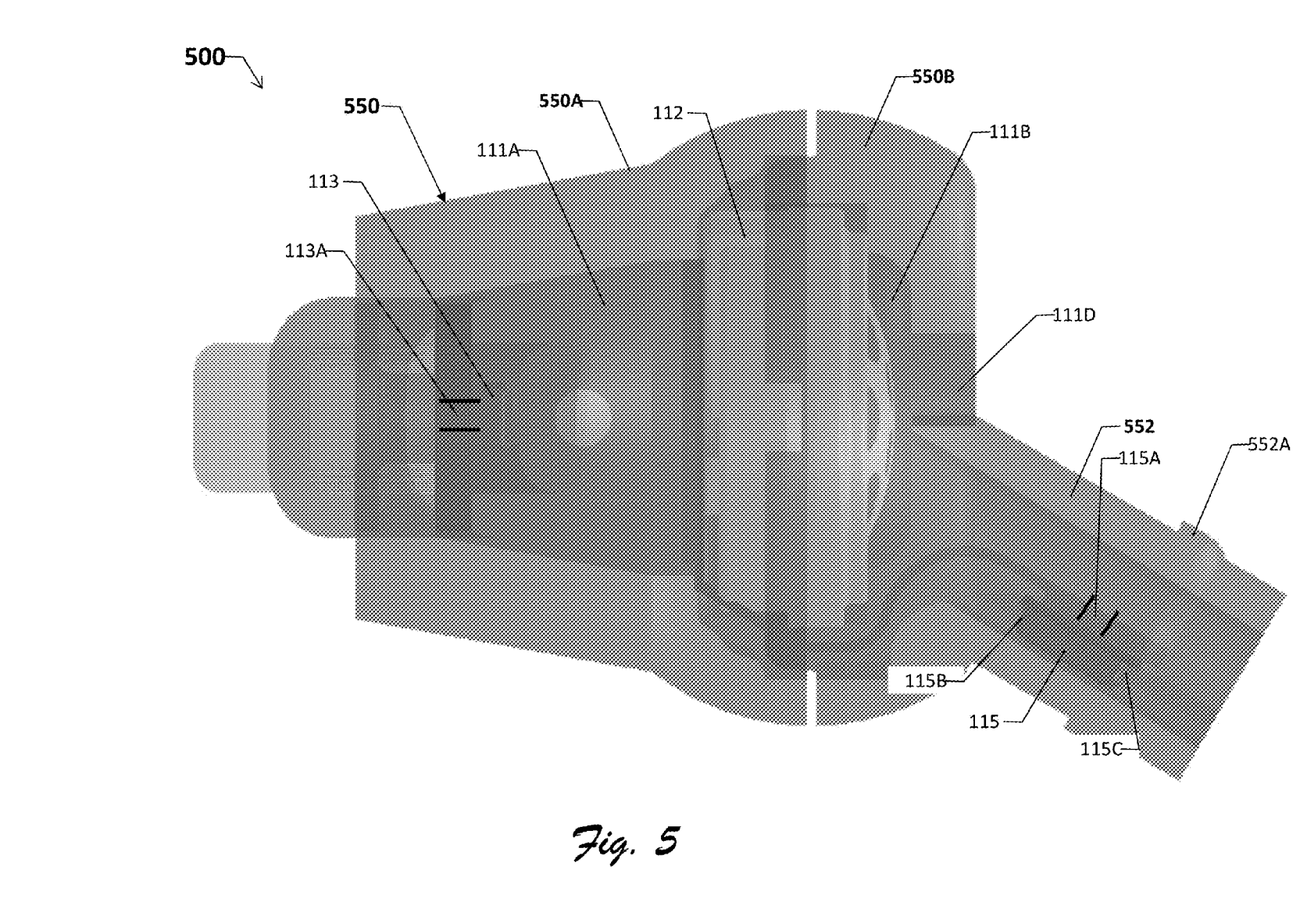
FIG. 5 is a profile view of an exemplary earphone assembly 500, corresponding to one or more embodiments of the invention.
Figure 6:
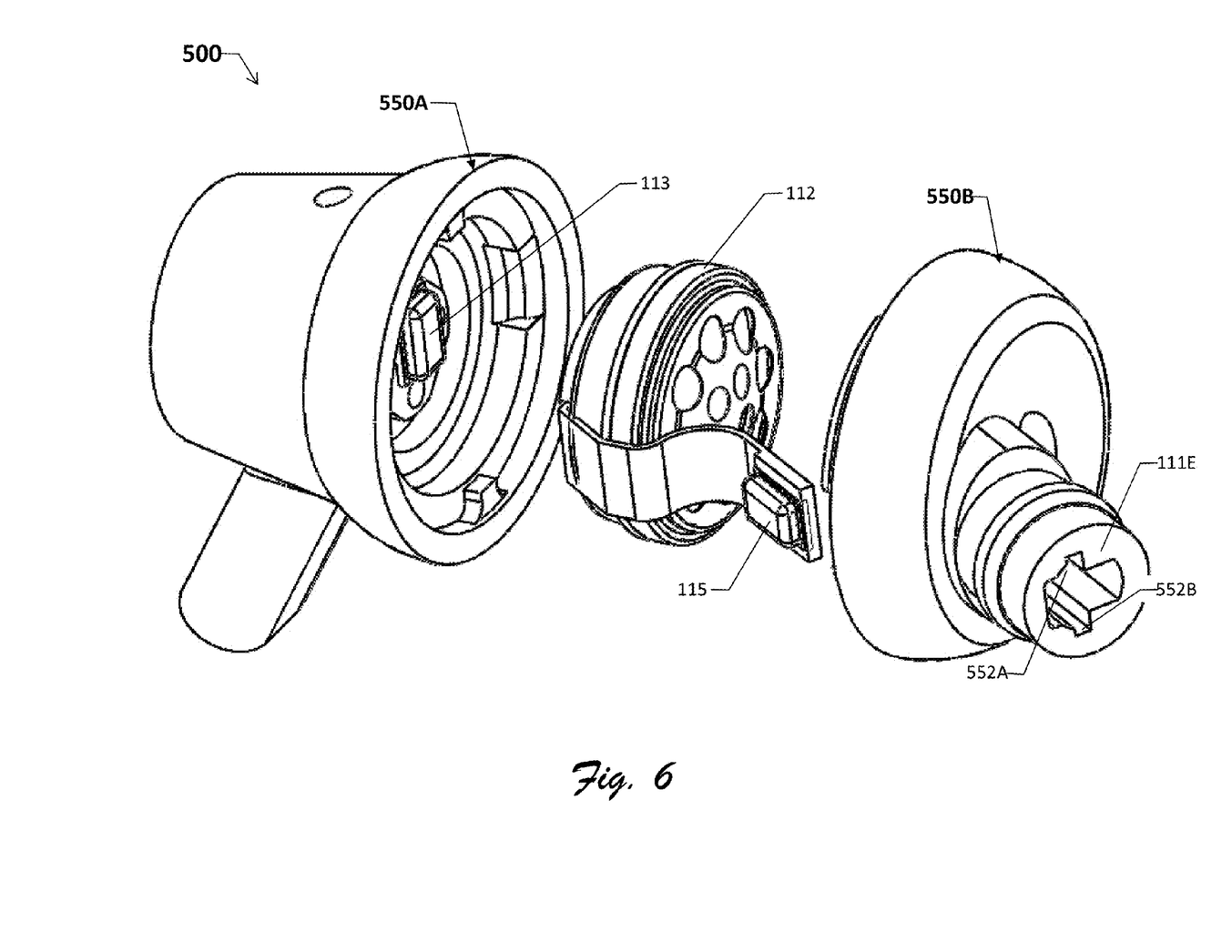
FIG. 6, is a partial exploded view of the FIG. 5 earphone assembly.
Figure 7:
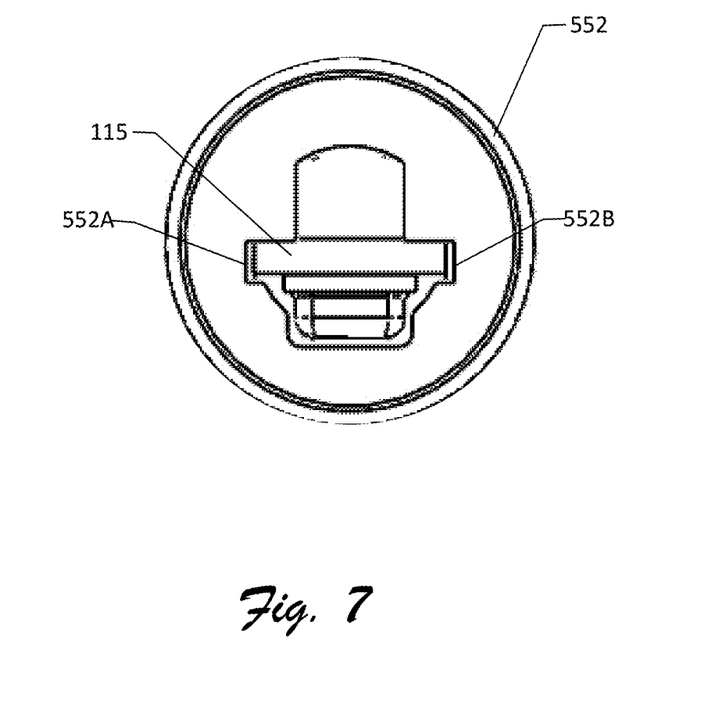
FIG. 7 is an end view of an ear nozzle portion of the FIG. 5 assembly

FIGS. 5, 6, and 7 show various aspects of an exemplary earpiece or earbud assembly 500 embodying operating principles of earpiece 120A,B as well as many identical or analogous components. Specifically, FIGS. 5 and 6 show that earpiece assembly 500 includes a housing 550 comprising respective back and front portions 550A and 550B which mate together around ANR driver 112. Back portion 550A includes, among other elements of earpiece 120A, feedforward ambient microphone 113, specifically a MEMS microphone. Front portion 550A includes an angled ear nozzle portion 552, analogous to nozzle 111E, with ear nozzle portion 552 includes a MEMS form of feedback error microphone 115 that includes microphone port 115A and opposing side flanges 115B and 115C. FIG. 7, a front view of nozzle portion 552, shows that flanges 115B and 115C engage slideably with corresponding opposing slots or grooves 552A and 552B formed in the interior surface of nozzle portion 552, ensuring perpendicular orientation of the microphone 115 to acoustic energy passing through nozzle portion 552.

CONCLUSION

In the foregoing specification, specific exemplary embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms, such as second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed. Also, the term "exemplary" is used as an adjective herein to modify one or more nouns, such as embodiment, system, method, device, and is meant to indicate specifically that the noun is provided as a non-limiting example.

What is claimed is:

1. An in-the-ear automatic noise reduction (ANR) device assembly comprising:
    a housing containing an ANR driver, with the driver dividing an interior of the housing into a back cavity and a front cavity;
    an ear-insertion port having a first end acoustically coupled to the front cavity and a second end configured for insertion within the ear canal of a user, wherein the ear insertion port has an effective acoustic mass in a range of 2000 to 2500 kq/M4, with M defined as pL/A, where p is density of air, L is the effective length of the ear-insertion port, and A is the open cross-sectional area of the ear-insertion port; and
    an ANR feedback microphone positioned within the ear-insertion port.

2. The assembly of claim 1, wherein the effective length of the ear-insertion portion includes a user-removable canal-conforming and sealing adapter tip.

3. The assembly of claim 2, wherein the canal-conforming adapter tip comprises a polymeric foam or a silicone rubber.

4. The assembly of claim 3, wherein the adapter tip comprises a generally rigid interior tube and a layer of polymeric foam surrounding the tube.

5. The assembly of claim 1, wherein the ear-insertion port has an axial dimension, and the microphone is a micro electro mechanical sensor (MEMS) microphone oriented transverse to the axial dimension.

6. The assembly of claim 1, wherein the ear-insertion port has an open cross-sectional area less than 7 square millimeters.

7. The assembly of claim 6, wherein the open cross-sectional area is less than 4 square millimeters.

8. The assembly of claim 1, wherein the port has a length of approximately 10 millimeters and the microphone is placed approximately at the midpoint of the port.

9. The assembly of claim 1, wherein the assembly further comprises:
an ANR processing circuit electrically coupled to the ANR driver and the ANR feedback microphone.

10. The assembly of claim 9, wherein the housing includes back cavity vent for the back cavity and a front cavity vent for the front cavity; and wherein the assembly further comprises an ambient feedforward microphone positioned on the housing and electrically coupled to the ANR processing circuitry, with the ANR processing circuitry including an adaptive filter coupled to the feedforward microphone.

11. An in-the-ear automatic noise reduction (ANR) device assembly comprising:
a housing containing an ANR driver, with the driver dividing an interior of the housing into a back cavity and a front cavity;
an ear-insertion port having a first end acoustically coupled to the front cavity and a second end configured for insertion within the ear canal of a user, with the second end including a conformal adapter tip configured to conform to the ear canal of a user and retain the housing adjacent the ear of a user, wherein the ear-insertion port has an effective acoustic mass in a range of 2000 to 2500 kq/M4, with M defined as pL/A, where p is density of air, L is the effective length of the ear-insertion port, and A is the open cross-sectional area of the ear-insertion port; and
an ANR feedback microphone positioned within the ear-insertion port; and ANR processing circuitry coupled to the ANR driver and ANR feedback port.

12. The assembly of claim 11, wherein the adapter tip comprises a polymeric foam or a silicone rubber.

13. The assembly of claim 11, wherein the adapter tip comprises a generally rigid interior tube and a layer of polymeric foam surrounding the tube.

14. The assembly of claim 11, wherein the ear-insertion port has an axial dimension, and the microphone is a micro electro mechanical sensor (MEMS) microphone oriented transverse to the axial dimension.

15. The assembly of claim 11, wherein the ear-insertion port has an open cross-sectional area less than 7 square millimeters.

16. The assembly of claim 15, wherein the open cross-sectional area is less than 4 square millimeters.

17. A method of operating an in-the-ear (ITE) automatic noise reduction (ANR) earphone having an ear-insertion port, the method comprising:
providing an ambient noise microphone coupled to ANR processing circuitry;
providing a feedback error microphone within the ear-insertion port, with the feedback error microphone coupled to the ANR processing circuitry;
wherein the ear-insertion port has an effective acoustic mass in a range of 2000 to 2500 kq/M4, with M defined as pL/A, where p is density of air, L is the effective length of the ear-insertion port, and A is the open cross-sectional area of the ear-insertion port; and
changing filter characteristics of a filter coupled to the feedforward microphone in response to at least one transfer function estimated using at least one of the ambient noise and feedback error microphones.

18. The method of claim 17, wherein the ear-insertion port has an axial dimension, and the feedback error microphone is a micro electro mechanical sensor (MEMS) microphone oriented transverse to the axial dimension.

19. The method of claim 17, wherein the open cross-sectional area is less than 4 square millimeters.

* * * * *